United States Patent [19]

Leca et al.

[11] 4,157,029
[45] Jun. 5, 1979

[54] RHEOMETER

[75] Inventors: Jean-Paul Leca, Mantes La Jolie; Alain Nardi, Bolbec, both of France

[73] Assignee: Societe Chimique des Charbonnages — CdF Chimie, Mazingarge, France

[21] Appl. No.: 849,593

[22] Filed: Nov. 8, 1977

[51] Int. Cl.² ............................................. B01N 11/04
[52] U.S. Cl. ............................................. 73/55
[58] Field of Search ............................... 73/55, 56

[56] References Cited

U.S. PATENT DOCUMENTS

| | | | |
|---|---|---|---|
| 2,934,944 | 5/1960 | Eolkin | 73/55 |
| 3,115,768 | 12/1963 | Rhodes et al. | 73/55 |
| 3,234,781 | 2/1966 | Bragg | 73/55 |
| 3,468,158 | 9/1969 | Sze-Foo Chien | 73/55 |
| 3,548,638 | 12/1970 | Uchida et al. | 73/55 |
| 3,559,464 | 2/1971 | Foust et al. | 73/55 |
| 3,938,369 | 2/1976 | deBok | 73/55 |

FOREIGN PATENT DOCUMENTS

| | | | |
|---|---|---|---|
| 1375862 | 11/1974 | United Kingdom | 73/55 |
| 395748 | 1/1974 | U.S.S.R. | 73/55 |
| 520537 | 8/1976 | U.S.S.R. | 73/55 |
| 524105 | 10/1976 | U.S.S.R. | 73/55 |

Primary Examiner—Jerry W. Myracle
Assistant Examiner—Joseph W. Roskos
Attorney, Agent, or Firm—Finnegan, Henderson, Farabow & Garrett

[57] ABSTRACT

The rheometer is located in a non-return branch of a molten polymer line and includes, in succession, a fixed-speed pump, a first capillary tube, and a second capillary tube in series with the first tube. The second tube has a diameter less than or equal to that of the first tube, and emerges into a fluid medium at regulated pressure. Pressure-sensors at the inlet of each tube determine the pressure loss between the inlet of each tube and the fluid medium at regulated pressure. The temperature is monitored by means that are at least party external to the body of the rheometer.

12 Claims, 1 Drawing Figure

U.S. Patent    Jun. 5, 1979    4,157,029
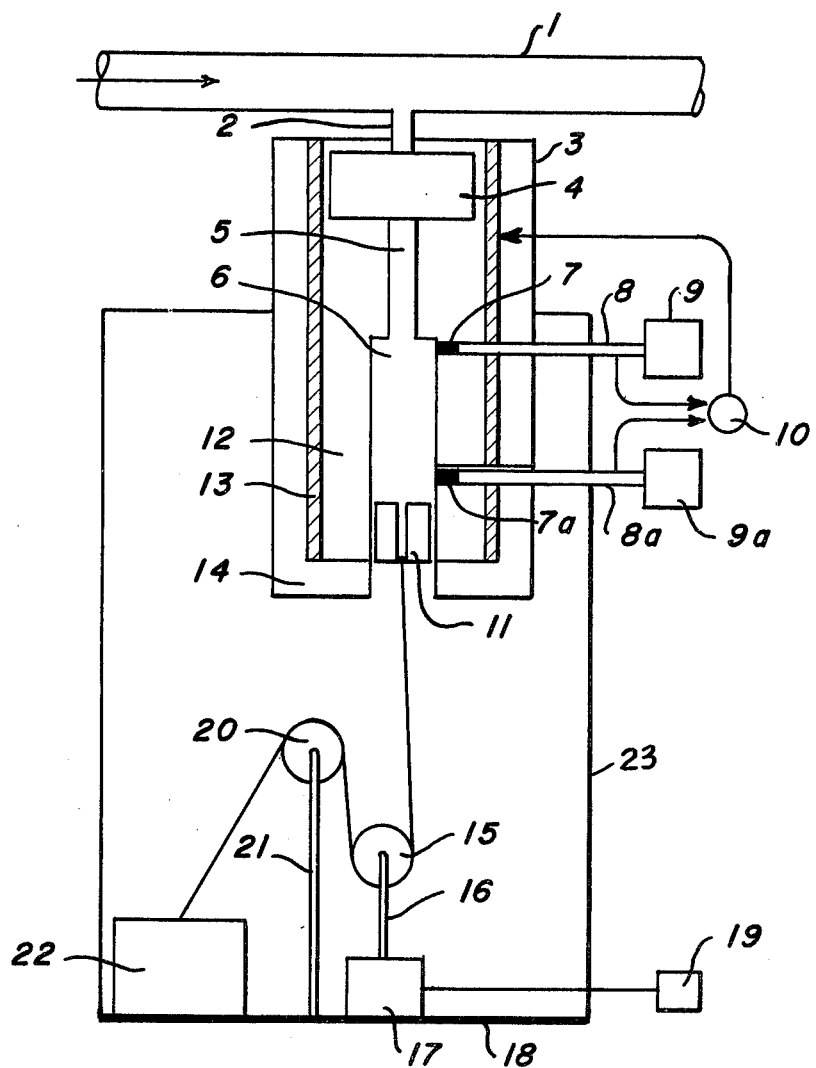

RHEOMETER

BACKGROUND OF THE INVENTION

The invention relates to a method of characterizing the rheological properties of a plastic material, and more particularly to a rheometer intended for the determination of the working-up capacity of a molten visco-elastic polymeric material.

It is known that information on the shear modulus and on the viscosity of a polymeric material is of extreme importance in characterizing commercial plastics, particularly thermo-plastics, since these properties determine the specific applications for which the plastics are intended. Thus, thermo-plastic resins intended for extrusion have visco-elastic properties which are very different from those intended for injection-moulding.

These rheological phenomena have already given rise to the study and development of apparatuses capable of providing data, the interpretation of which makes it possible to calculate the desired properties. Thus U.S. Pat. No. 3,559,464 describes a rheometer for continuous monitoring, arranged in parallel with the main polymer flow line and comprising (a) a heat-controlled block provided with a first capillary tube and with a second capillary tube of the same diameter but of a greater length than the first tube, (b) a pump of variable speed connected to the block and inserted between the two capillaries, and (c) differential pressure gauges fitted on the capillaries. This device constitutes a pressure regulation system which is intricate and difficult to maintain, and suffers the disadvantage of allowing measurement of the rheological properties for only a single shear-level of the visco-elastic material. From this standpoint it therefore provides incomplete results and allows only an approximate determination of the working-up capacity of the polymers.

A first object of the inventon is therefore to provide an apparatus which can, by measurements at different shear-levels, determine with great precision the working-up capacity of a molten visco-elastic polymeric material. A second object of the invention is, when a lesser precision in the determination of the rheological behavior of a polymer is acceptable, to provide an apparatus whose construction and maintenance are easier than those of known apparatuses and which can more easily be adapted to the direct and speedy monitoring of very large polymerization units.

SUMMARY OF THE INVENTION

To achieve the foregoing objects and in accordance with the purpose of the invention, as embodied and broadly described herein, the rheometer of this invention is arranged in a non-return branch of a molten polymer line and comprises (1) a body including a fixed-speed pump, a first capillary tube downstream of the pump, a second capillary tube in series with the first capillary tube and of a diameter less than or equal to that of the first tube, the second tube emerging in a fluid medium at regulated pressure, and a pressure-sensor fitted at the inlet of each tube in order to measure the pressure loss between the inlet of each tube and the fluid medium at regulated pressure, and (2) means for monitoring the temperature which are at least partly external to the body.

If the process of preparation of the polymer involves the presence of molten polymer in the polymerization plant, the rheometer of the invention can be located in this part of the plant. In ethylene polymerization plants under high pressure, the rheometer will be connected to the outlet of the separator.

This apparatus is useful for rheological information on very diverse polymers, e.g., polystyrene and all polyolefins, namely low and high density polyethylenes, polypropylene, and polybutene. As usual in this technique, the external part of the temperature monitoring means includes appropriate isothermic and adiabatic jackets, whose purpose is to keep the temperature of the molten visco-elastic material circulating in the body constant. The fluid medium at regulated pressure is situated at the outlet of the second capillary tube and is generally a gaseous medium such as air at atmospheric pressure; it can also be an inert gaseous medium, such as nitrogen or argon, where it is necessary to evaluate or measure other properties, for example chemical properties, of the polymer at the outlet of the rheometer. It should be noted that the components of the rheometer according to the invention, i.e., the fixed-speed pump and the pressure-sensors functioning with reference to a known pressure, are of simpler design and are easier to maintain than those incorporated in the apparatus of U.S. Pat. No. 3,559,464.

According to a preferred embodiment of the invention, the temperature monitoring means of the rheometer comprise not only the external part discussed above, but also a part inside the body, this part being arranged between the fixed-speed pump and the first capillary tube. This internal part may comprise, for example, a tubular heat-exchange zone. The diameter of this zone should be as small as possible in order to promote the efficiency of this heat-exchange. However, the choice of this diameter is limited by the absolute necessity of avoiding any rheological modification of the polymer, such as the so-called melt-fracture phenomenon, during its flow through the tubular heat-exchange zone.

An example of the possibility, indicated above, of carrying out a supplementary characterization of the working-up capacity of the polymer at the outlet of the rheometer is means rigidly fastened to the body of the rheometer for measuring the extensibility of the polymer in the molten state. As embodied herein, this means comprises, for example, a strip extensometer. This embodiment is described below and illustrated in the drawing.

If great precision is required in the determination of the rheological behavior of the visco-elastic material, the rheometer of the invention must be able to provide measurements at various shear levels. For this purpose, its second capillary tube is arranged immediately in series with the first capillary tube and has a diameter which must be less than that of the latter. Preferably, the shear speed gradient in the first capillary tube is between 0.1 and 50 seconds$^{-1}$ and the shear speed gradient in the second capillary tube is between 100 and 5,000 seconds$^{-1}$. Furthermore, since the pressures measured by the pressure-sensors of the rheometer body are related to the length and to the diameter of the capillary tubes, and since, for reasons of convenience and reliability, it is desirable to measure pressures of the same order of magnitude, the length of the first capillary tube should preferably be much greater than that of the second tube. The second capillary tube may be removable and replaceable with a tube of another diameter and the first capillary tube may be linable to vary its diameter, in order to adapt the apparatus to the flow of resins having very different rheological characteristics (especially the melt index), as frequently occurs in very large capacity polymerization units.

The accompanying drawing, which is incorporated in and constitutes a part of this Specification, illustrates one embodiment of the invention and, together with the description, serves to explain the principles of the invention.

BRIEF DESCRIPTION OF THE DRAWING

The drawing is a schematic diagram of a rheometer constructed in accordance with the present invention.

DESCRIPTION OF THE PREFERRED EMBODIMENT

Reference will now be made in detail to the present preferred embodiment of the invention, an example of which is illustrated in the accompanying drawing.

The invention will be better understood by reference to the single figure, which represents schematically the rheometer with a double shear level, including, as embodied herein, a device for measuring the extensibility of the polymer in the molten state. In this figure, 1 denotes the main flow line of a polymer, for example the outlet line of a separator of a manufacturing unit of the polymer, from which a branch 2 conducts the visco-elastic material to the body 3 of a rheometer. As embodied herein, the body comprises successively a fixed-speed pump 4, a tubular heat-exchange zone 5, and a first capillary tube 6. In accordance with the invention, this tube is provided with pressure and temperature sensors 7 and 7a at its inlet and at its outlet, which sensors are arranged in housings 8 and 8a and connected firstly to pressure recorders 9 and 9a and secondly to an electronic temperature-regulating system 10. The second capillary tube 11, like the zone 5 and the first tube 6, is located in a metal part 12 which is itself surrounded by a heating jacket 13, the operation of which is controlled by the system 10, the assembly being surrounded by an insulating jacket 14 made, for example, of glass-wool and/or asbestos. As embodied herein, after flowing through the capillary tubes, the strip of molten polymer arrives tangentially to the detection pulley 15 of the device for measuring the extensibility, also called an extensometer. This pulley is firmly fixed, via a rod 16, to a force sensor 17, which is fixed to a carrier-plate 18 and connected electrically to a recorder 19 by an adjustable free-rotating pulley. The carrier 18, while being thermally insulated from the body 3 of the rheometer, is linked mechanically to it by any connecting means 23, such as a rod or plate, allowing easy dispersal of the heat given off in this area by the polymer strip. If desired to increase the precision of the measurement of the drawing force, the strip is passed over a second pulley 20 which is firmly fixed, via a rod 21, to the carrier-plate 18. The strip, held by these pulleys, is drawn by a fixed speed drawing-bench 22, for example of the compact type consisting of a synchronous motor and a gear box equipped with rubberized drawing pulleys.

Reconsidering the various uses of the invention, if ordinary precision is sufficient for the determination of the rheological behavior of the visco-elastic material, the rheometer of the invention can carry out measurements at a single shear level. Its second capillary tube is then provided with the same diameter as the first tube and is not arranged immediately in series with the latter, but is separated therefrom by a perforated distance-piece having a diameter greater than the diameter of the capillary tubes, in order to allow relaxation of the visco-elastic material between said tubes. Furthermore, in this embodiment, the length of the first capillary tube is preferably at least twice that of the second tube.

Although the present invention has been described by means of preferred embodiments, it will be apparent to those skilled in the art that various modifications and variations can be made in the rheometer of the invention without departing from the scope or spirit of the invention. For example, the rheometer may carry out measurements at n different shear levels, n being greater than 2, by including, in series, n capillary tubes with decreasing diameters and provided with n pressure-sensors.

What is claimed is:

1. A rheometer for the continuous determination of the working-up capacity of a molten visco-elastic polymeric material, comprising:
   (i) a non-return branch connected to a molten polymer line;
   (ii) a fluid medium at regulated pressure;
   (iii) a body, connected in series to and between said non-return branch and said fluid medium, including a fixed-speed pump, a first capillary tube situated downstream of said pump, a second capillary tube in series with said first tube and of a diameter less than or equal to that of said first tube, said second tube emerging in said fluid medium, and a pressure-sensor fitted at the inlet of each tube in order to measure the pressure loss between the inlet of each tube and the fluid medium; and
   (iv) means for monitoring the temperature which are at least partly external to said body.

2. The rheometer of claim 1, wherein said means for monitoring the temperature comprise a part, inside the body, which is arranged between said fixed-speed pump and said first capillary tube.

3. The rheometer of claim 2, wherein said internal part of said means for monitoring the temperature comprises a tubular heat-exchange zone of diameter such that the visco-elastic material is not subjected to any rheological modification therein.

4. The rheometer of claim 1, further comprising, fastened rigidly to said body, means for measuring the extensibility in the molten state of the visco-elastic polymeric material.

5. The rheometer of claim 1, wherein said second capillary tube is arranged immediately in series with said first tube and is of a diameter less than that of said first tube, in order to create separate shear speed gradients in said first and second tubes.

6. The rheometer of claim 5, wherein the length of said first capillary tube is much greater than that of said second tube.

7. The rheometer of claim 5, wherein the shear speed gradient in said first capillary tube is between 0.1 and 50 seconds$^{-1}$ and the shear speed gradient in said second capillary tube is between 100 and 5,000 seconds$^{-1}$.

8. The rheometer of claim 5, wherein said second capillary tube is removable.

9. The rheometer of claim 8, wherein said first capillary tube can be lined.

10. The rheometer of claim 1, wherein said second capillary tube is connected to said first tube by a distance-piece and is of a diameter equal to that of said first tube.

11. The rheometer of claim 10, wherein the length of said first tube is at least twice that of said second tube.

12. The rheometer of claim 1, wherein said molten polymer line is the outlet line of the separator of an ethylene polymerization plant under high pressure.

* * * * *